(12) United States Patent
Lindsay et al.

(10) Patent No.: US 12,296,121 B2
(45) Date of Patent: May 13, 2025

(54) DRAINAGE CATHETER

(71) Applicant: Merit Medical Systems, Inc., South Jordan, UT (US)

(72) Inventors: Richard Lindsay, Northern Ireland (GB); Denise Hallisey, Wethersfield, CT (US); Nicholas Accisano, III, Howell, NJ (US); David Butts, Riverton, UT (US); F. Mark Ferguson, Salt Lake City, UT (US); Kirk Loren Foote, Cottonwood Heights, UT (US); Mark Garcia, Wilmington, DE (US); Gregory R. McArthur, Sandy, UT (US); Kenneth Sykes, Bluffdale, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 966 days.

(21) Appl. No.: 15/802,160

(22) Filed: Nov. 2, 2017

(65) Prior Publication Data

US 2018/0117288 A1 May 3, 2018

Related U.S. Application Data

(60) Provisional application No. 62/500,900, filed on May 3, 2017, provisional application No. 62/416,960, filed on Nov. 3, 2016.

(51) Int. Cl.
*A61M 27/00* (2006.01)
*A61M 25/00* (2006.01)
(Continued)

(52) U.S. Cl.
CPC ...... *A61M 27/002* (2013.01); *A61M 25/0041* (2013.01); *A61M 25/0045* (2013.01);
(Continued)

(58) Field of Classification Search
CPC .. A61M 2025/0008; A61M 2025/0046; A61M 2039/1061; A61M 2039/1072;
(Continued)

(56) References Cited

U.S. PATENT DOCUMENTS

| 1,207,479 A | 12/1916 | Bisgaard |
|---|---|---|
| 3,924,633 A | 12/1975 | Cook et al. |

(Continued)

FOREIGN PATENT DOCUMENTS

| EP | 0609020 | 8/1994 |
|---|---|---|
| WO | 199916355 | 4/1999 |

(Continued)

OTHER PUBLICATIONS

International Search Report and Written Opinion dated May 30, 2018 for PCT/US2017/059757.
(Continued)

*Primary Examiner* — Kai H Weng
*Assistant Examiner* — Alessandro R Del Priore
(74) *Attorney, Agent, or Firm* — Dorsey & Whitney LLP

(57) ABSTRACT

The present disclosure relates to a drainage catheter and methods of use for providing catheterization procedures, such as during a percutaneous nephrostomy. The drainage catheter includes a body including a first tube segment and a second tube segment connected to one another at a curved end portion to form a continuous body structure. An inner surface of the curved end portion includes one or more drainage openings extending therethrough, with an outer surface of the curved end portion free of drainage openings. The openings are in communication with a lumen that extends through the drainage catheter to provide a pathway for removing fluid from the kidney. The drainage catheter is inserted into the kidney via a first insertion site and exits via a second insertion site.

11 Claims, 8 Drawing Sheets

(51) Int. Cl.
*A61M 25/01* (2006.01)
*A61M 39/10* (2006.01)

(52) U.S. Cl.
CPC ...... *A61M 25/007* (2013.01); *A61M 25/0108* (2013.01); *A61M 27/00* (2013.01); *A61M 39/105* (2013.01); *A61M 2025/0008* (2013.01); *A61M 2025/0046* (2013.01); *A61M 25/0113* (2013.01); *A61M 2039/1061* (2013.01); *A61M 2039/1072* (2013.01); *A61M 2205/0216* (2013.01); *A61M 2210/1082* (2013.01)

(58) Field of Classification Search
CPC .. A61M 2205/0216; A61M 2210/1082; A61M 25/0041; A61M 25/0045; A61M 25/007; A61M 25/0108; A61M 25/0113; A61M 27/00; A61M 27/002; A61M 39/105; A61M 25/0029; A61M 2025/0163; A61M 25/01; A61B 2090/062; A61F 2250/0097
See application file for complete search history.

(56) References Cited

U.S. PATENT DOCUMENTS

| | | | |
|---|---|---|---|
| 4,230,122 A | 10/1980 | Lubbers et al. | |
| 4,573,981 A | 3/1986 | McFarlane | |
| 4,586,923 A | 5/1986 | Gould et al. | |
| 4,593,698 A | 6/1986 | Athans | |
| 4,643,720 A | 2/1987 | Lanciano | |
| 4,738,667 A | 4/1988 | Galloway | |
| 4,740,195 A | 4/1988 | Lanciano | |
| 4,787,892 A | 11/1988 | Rosenberg | |
| 4,867,745 A | 9/1989 | Patel | |
| 4,885,503 A | 12/1989 | Takahashi et al. | |
| 4,986,279 A * | 1/1991 | O'Neill | A61B 90/39 |
| | | | 600/567 |
| 5,019,054 A | 5/1991 | Clement et al. | |
| 5,052,998 A | 10/1991 | Zimmon | |
| 5,078,684 A | 1/1992 | Yasuda | |
| 5,213,575 A | 5/1993 | Scotti | |
| 5,224,935 A | 7/1993 | Hollands | |
| 5,308,318 A | 5/1994 | Plassche, Jr. | |
| 5,336,177 A * | 8/1994 | Marcus | A61M 27/00 |
| | | | 604/264 |
| 5,352,198 A | 10/1994 | Goldenberg et al. | |
| 5,399,165 A | 3/1995 | Paul, Jr. | |
| 5,419,764 A | 5/1995 | Roll | |
| 5,472,435 A * | 12/1995 | Sutton | A61M 25/005 |
| | | | 604/540 |
| 5,489,269 A | 2/1996 | Aldrich et al. | |
| 5,506,202 A | 4/1996 | Blackman et al. | |
| 5,522,400 A | 6/1996 | Williams | |
| 5,531,741 A | 7/1996 | Barbacci | |
| 5,666,970 A | 9/1997 | Smith | |
| 5,693,083 A | 12/1997 | Baker et al. | |
| 5,704,926 A | 1/1998 | Sutton | |
| 5,730,724 A | 3/1998 | Plishka et al. | |
| 5,730,730 A | 3/1998 | Darling, Jr. | |
| 5,827,249 A | 10/1998 | Jensen | |
| 5,893,880 A | 4/1999 | Egan et al. | |
| 5,904,648 A | 5/1999 | Arndt et al. | |
| 5,941,849 A | 8/1999 | Plassche, Jr. | |
| 6,159,177 A | 12/2000 | Amos et al. | |
| 6,165,183 A | 12/2000 | Kuehn et al. | |
| 6,178,342 B1 | 1/2001 | Borgos et al. | |
| 6,213,986 B1 | 4/2001 | Darling, Jr. | |
| 6,231,542 B1 | 5/2001 | Amos et al. | |
| 6,358,271 B1 | 3/2002 | Egan et al. | |
| 6,454,740 B1 | 9/2002 | Mody | |
| 6,508,789 B1 | 1/2003 | Sinnott et al. | |
| 6,547,761 B2 | 4/2003 | Liu | |
| 6,673,060 B1 | 1/2004 | Fliming, III | |
| 6,699,233 B2 * | 3/2004 | Slanda | A61M 25/00 |
| | | | 604/533 |
| 6,997,951 B2 | 2/2006 | Solem et al. | |
| 7,087,038 B2 | 8/2006 | Lee | |
| 7,217,256 B2 | 5/2007 | Di Palma | |
| 7,338,475 B2 | 3/2008 | Brown | |
| 7,578,814 B2 | 8/2009 | Accisano et al. | |
| 7,618,398 B2 | 11/2009 | Holman et al. | |
| 7,641,630 B2 | 1/2010 | Accisano, III et al. | |
| 8,876,789 B1 * | 11/2014 | Getsay | A61M 5/00 |
| | | | 604/317 |
| 2003/0214408 A1 | 11/2003 | Grajales et al. | |
| 2004/0059293 A1 | 3/2004 | Chu et al. | |
| 2005/0070821 A1 | 3/2005 | Deal et al. | |
| 2005/0107739 A1 | 5/2005 | Di Palma | |
| 2005/0203485 A1 | 9/2005 | Lee | |
| 2005/0261663 A1 * | 11/2005 | Patterson | A61M 25/0068 |
| | | | 604/508 |
| 2006/0009759 A1 * | 1/2006 | Christian | A61B 18/1492 |
| | | | 606/41 |
| 2006/0129111 A1 | 6/2006 | Mottola | |
| 2006/0206096 A1 | 9/2006 | Accisano et al. | |
| 2006/0212009 A1 | 9/2006 | Accisano et al. | |
| 2006/0217667 A1 | 9/2006 | Accisano et al. | |
| 2007/0032779 A1 | 2/2007 | Accisano et al. | |
| 2007/0078385 A1 | 4/2007 | Accisano et al. | |
| 2007/0083189 A1 | 4/2007 | Lampropoulos | |
| 2008/0009804 A1 * | 1/2008 | Rosetti | A61M 25/0071 |
| | | | 604/173 |
| 2008/0097394 A1 | 4/2008 | Lampropoulos et al. | |
| 2010/0049171 A1 * | 2/2010 | McQueen | A61M 25/0041 |
| | | | 604/540 |
| 2010/0070047 A1 | 3/2010 | Smouse | |
| 2011/0098524 A1 | 4/2011 | Barcelo Rojas | |
| 2012/0172822 A1 | 7/2012 | Gilman | |
| 2012/0256020 A1 | 10/2012 | Pandey et al. | |
| 2012/0265020 A1 | 10/2012 | Pandey et al. | |
| 2014/0058251 A1 * | 2/2014 | Stigall | A61B 1/05 |
| | | | 600/424 |
| 2014/0228801 A1 * | 8/2014 | Keeling | A61M 25/0023 |
| | | | 604/500 |
| 2015/0283357 A1 | 10/2015 | Lampropoulos et al. | |
| 2017/0014598 A1 * | 1/2017 | Stursa | A61M 25/005 |
| 2017/0021139 A1 * | 1/2017 | Bajema | A61B 17/3207 |
| 2017/0303940 A1 * | 10/2017 | Sperry | A61B 17/3417 |
| 2018/0221649 A1 * | 8/2018 | Mulrooney | A61B 90/08 |
| 2019/0008551 A1 * | 1/2019 | Entabi | A61B 17/3474 |

FOREIGN PATENT DOCUMENTS

| | | |
|---|---|---|
| WO | 200176675 | 10/2001 |
| WO | 2003097127 | 11/2003 |
| WO | 2006098818 | 9/2006 |
| WO | 2006098819 | 9/2006 |
| WO | 2006101592 | 9/2006 |
| WO | 2007019074 | 2/2007 |
| WO | WO-2016191062 A2 * | 12/2016 ....... A61B 17/00234 |

OTHER PUBLICATIONS

Angiodynamics, Abscession Drainage Catheter: A Quick Guide to the Locking Mechanism, AngioDynamics, Inc., Nov. 1999.
International Search Report and Written Opinion dated Feb. 21, 2007 for PCT/US2006/029304.
International Search Report and Written Opinion dated Jun. 14, 2006 for PCT/US2006/03467.
International Search Report and Written Opinion dated Jul. 26, 2007 for PCT/US2006/003464.
International Search Report and Written Opinion dated Sep. 18, 2007 for PCT/US2006/003021.
Notice of Allowance date Jun. 16, 2010 for U.S. Appl. No. 11/205,609.
Notice of Allowance dated Jan. 7, 2011 for U.S. Appl. No. 12/557,348.
Notice of Allowance dated Jan. 26, 2010 for U.S. Appl. No. 11/078,939.
Notice of Allowance dated Feb. 5, 2010 for U.S. Appl. No. 11/608,518.
Notice of Allowance dated Mar. 19, 2010 for U.S. Appl. No. 11/205,609.

(56) References Cited

OTHER PUBLICATIONS

Notice of Allowance dated Apr. 20, 2009 for U.S. Appl. No. 11/198,642.
Notice of Allowance dated Jul. 27, 2009 for U.S. Appl. No. 11/608,518.
Notice of Allowance dated Aug. 5, 2009 for U.S. Appl. No. 11/078,939.
Notice of Allowance dated Oct. 13, 2009 for U.S. Appl. No. 11/078,140.
Notice of Allowance dated Nov. 6, 2015 for U.S. Appl. No. 11/507,777.
Office Action dated Mar. 3, 2009 for U.S. Appl. No. 11/078,140.
Office Action dated Mar. 10, 2009 for U.S. Appl. No. 11/081,301.
Office Action dated Apr. 23, 2014 for U.S. Appl. No. 11/507,777.
Office Action dated May 6, 2009 for U.S. Appl. No. 11/507,777.
Office Action dated May 7, 2015 for U.S. Appl. No. 11/507,777.
Office Action dated May 21, 2008 for U.S. Appl. No. 11/078,939.
Office Action dated May 28, 2008 for U.S. Appl. No. 11/078,140.
Office Action dated Jun. 26, 2008 for U.S. Appl. No. 11/081,301.
Office Action dated Jul. 14, 2010 for U.S. Appl. No. 12/557,348.
Office Action dated Jul. 20, 2009 for U.S. Appl. No. 11/205,609.
Office Action dated Sep. 4, 2008 for U.S. Appl. No. 11/198,642.
Office Action dated Sep. 9, 2009 for U.S. Appl. No. 11/507,777.
Office Action dated Oct. 16, 2008 for U.S. Appl. No. 11/608,518.
Office Action dated Oct. 23, 2007 for U.S. Appl. No. 11/081,301.
Office Action dated Oct. 23, 2014 for U.S. Appl. No. 11/507,777.
European Search Report dated Jun. 9, 2020 for EP17867517.9.
Extended European Search Report dated Sep. 10, 2020 for EP17867517.9.

\* cited by examiner

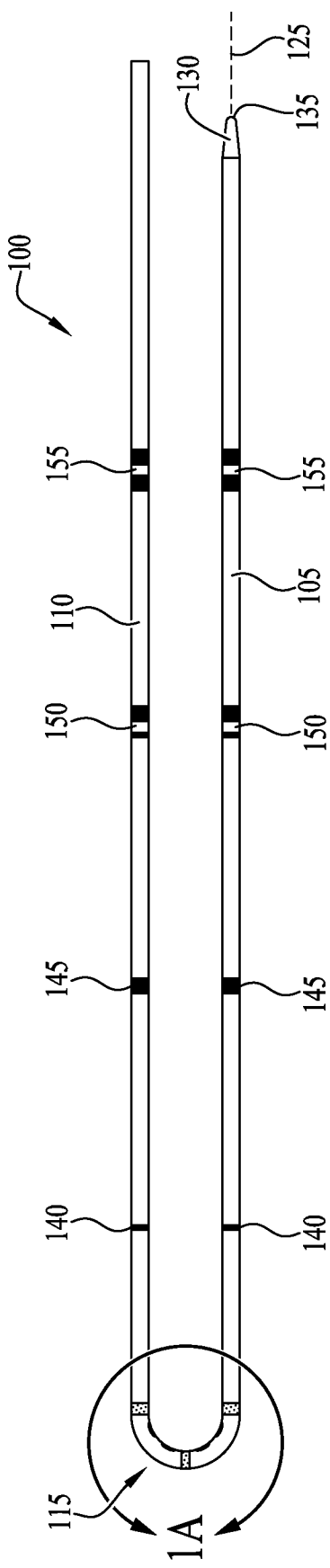
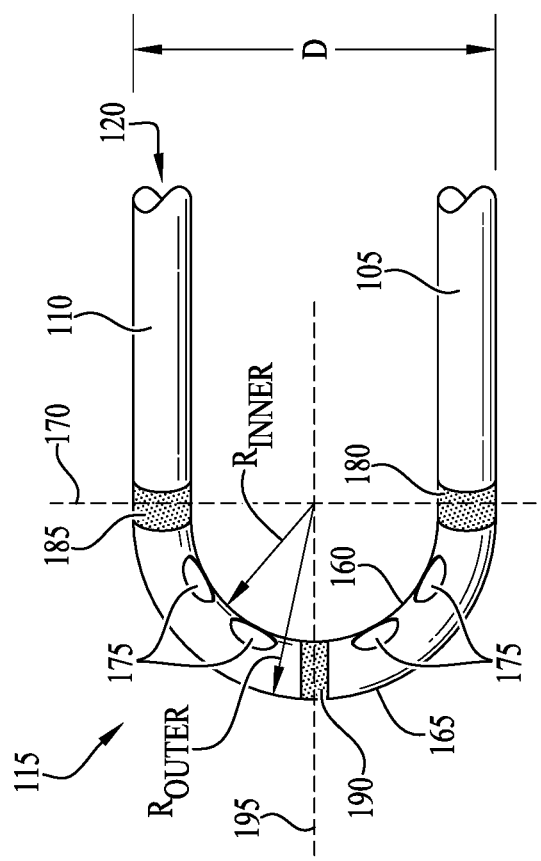
Fig. 1
Fig. 1A

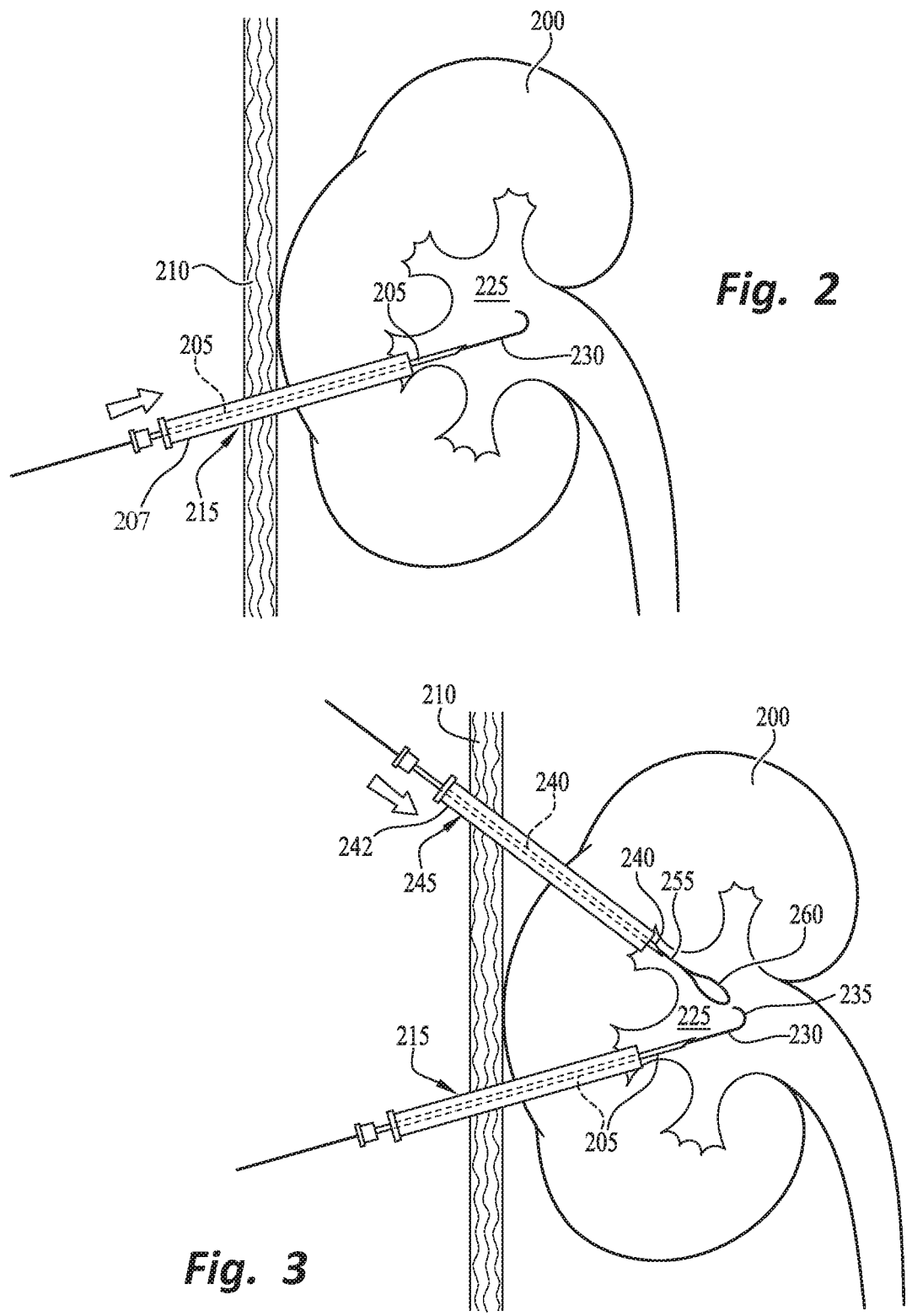

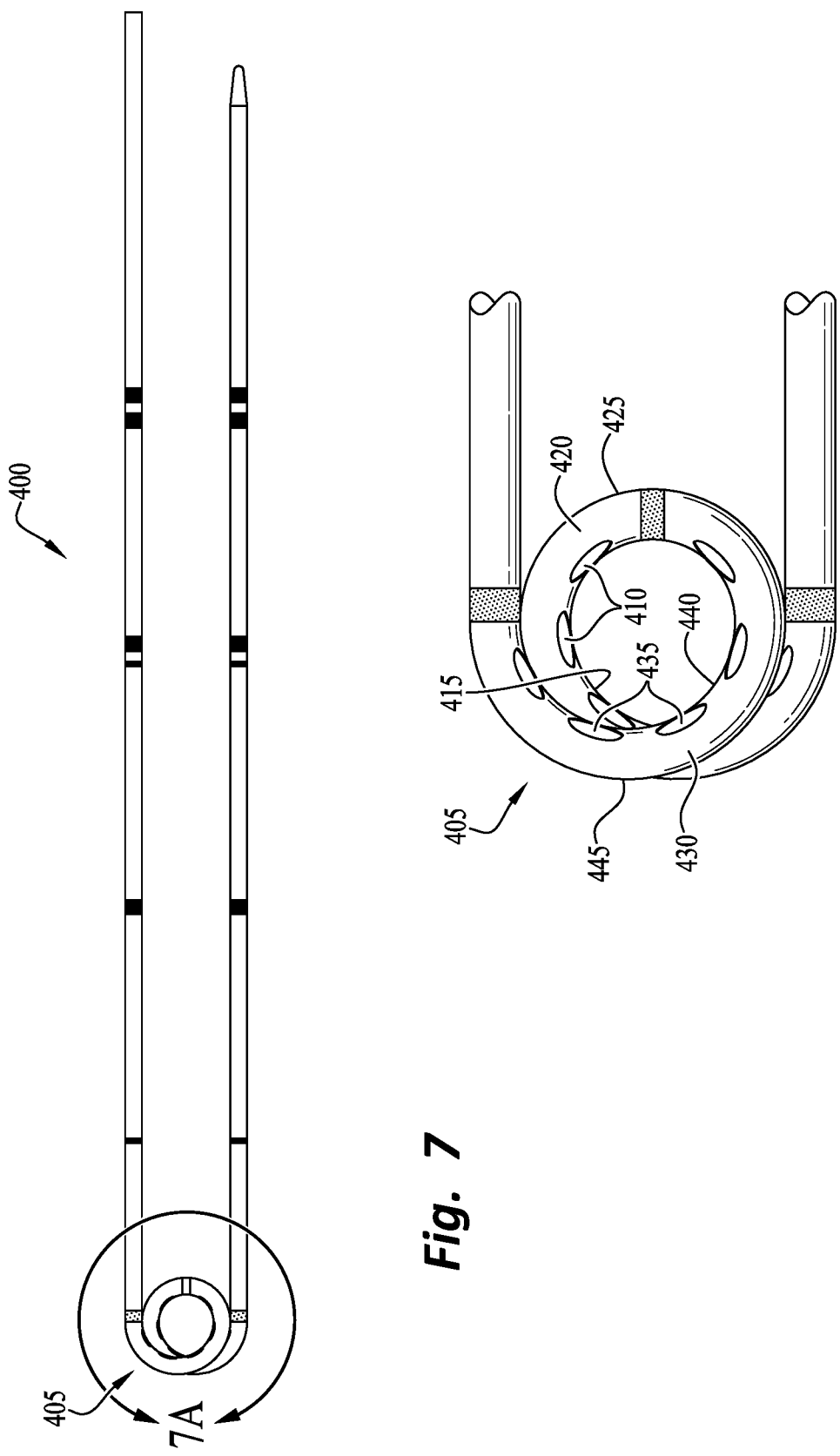

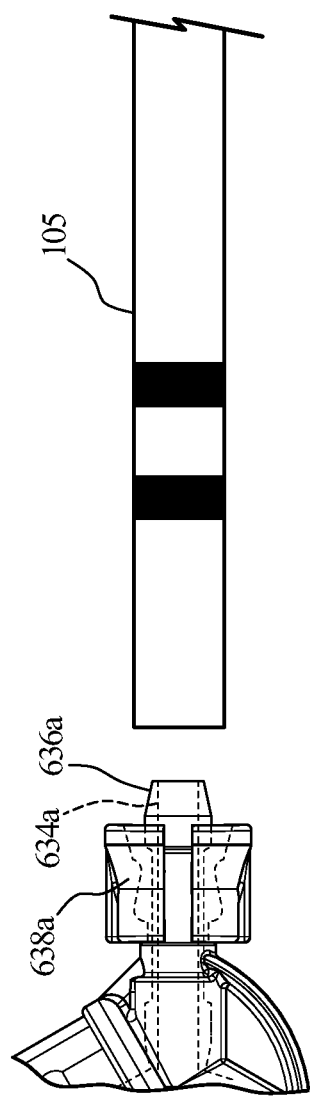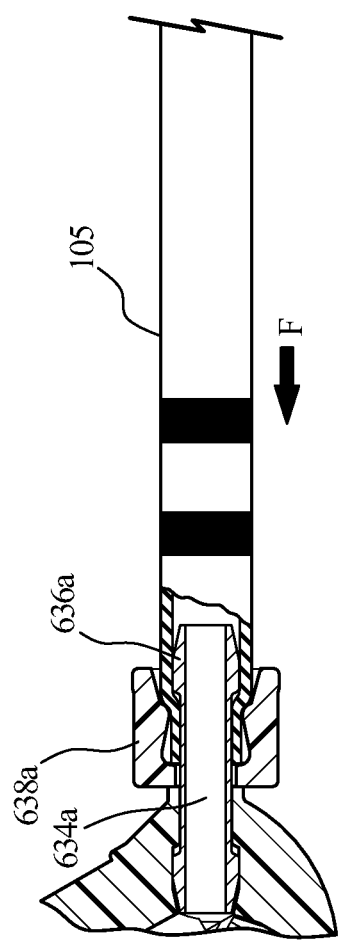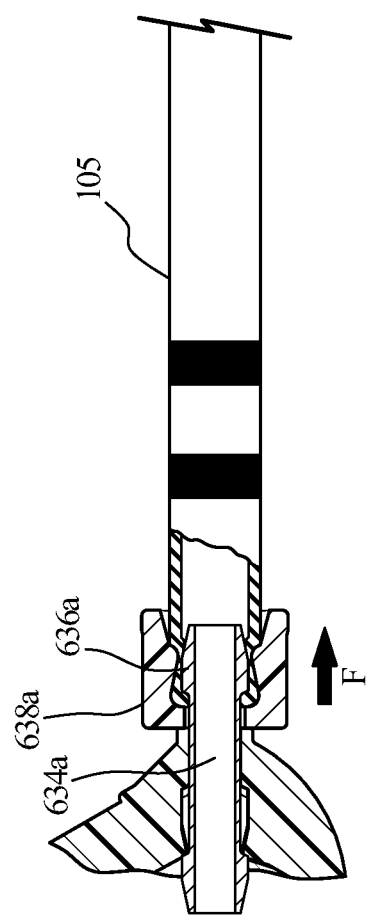

DRAINAGE CATHETER

RELATED APPLICATIONS

This application claims priority to U.S. Provisional Application No. 62/416,960, filed Nov. 3, 2016, and titled "Drainage Catheter" and claims priority to U.S. Provisional Application No. 62/500,900, filed May 3, 2017, and titled "Drainage Catheter" both of which are hereby incorporated by reference in their entireties.

TECHNICAL FIELD

The present disclosure relates generally to drainage catheters for medical use. More specifically, the present disclosure relates to a looped drainage catheter designed for improved drainage and to minimize risks of accidental removal. Related methods of use are also disclosed.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

FIG. 1 illustrates a view of a looped drainage catheter in accordance with one exemplary embodiment.

FIG. 1A illustrates an expanded view of an end portion of the looped drainage catheter of FIG. 1.

FIG. 2 illustrates a first needle and first guidewire positioned in the renal pelvis of the kidney.

FIG. 3 illustrates a second needle and second guidewire having a snare to couple with the first guidewire.

FIG. 7 illustrates a view of a coiled drainage catheter in accordance with another exemplary embodiment.

FIG. 7A illustrates an expanded view of an end portion of the coiled drainage catheter of FIG. 7.

FIG. 10A illustrates a side view of the break-way connector of FIG. 9 and a catheter.

FIG. 10B illustrates a side view of the break-away catheter of FIG. 9 coupled to a catheter.

FIG. 10C illustrates a side view of the break-away catheter of FIG. 9 coupled to a catheter.

DETAILED DESCRIPTION

Figure 4:
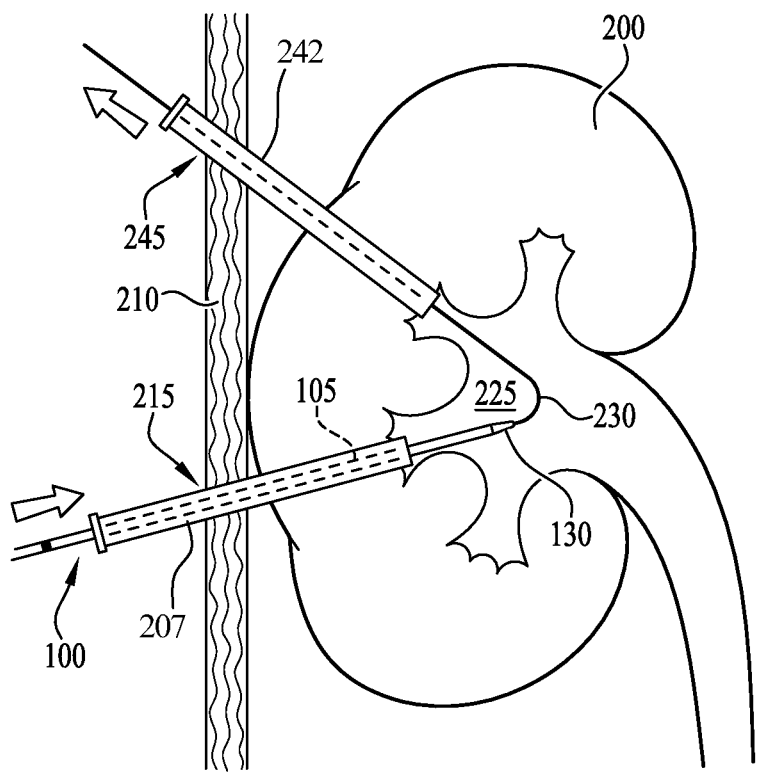
FIG. 4 illustrates the catheter of FIG. 1 partially advanced into the kidney over the first guidewire.

The various embodiments disclosed herein generally relate to drainage catheters and related methods of use. More specifically, the various embodiments relate to a drainage catheter that may be used for percutaneous nephrostomy or nephropyelostomy, a procedure used primarily to provide temporary drainage for an obstructed renal collecting system. In many cases, the obstructed area may become infected, and antibiotics are unable to penetrate the kidney when the obstruction cannot be drained. In such cases, percutaneous nephrostomy may be used to alleviate the obstruction and to create a route for antibiotic instillation, or other treatments, if needed. As is explained in further detail below, one advantage of the disclosed drainage catheter is its elasticity that allows the drainage catheter to be sufficiently pliable to minimize potential injury during insertion, but also sufficiently rigid to maintain a generally U-shape bend when deployed within the kidney to avoid clogging and promote drainage. Also disclosed herein are methods for inserting the drainage catheter into a patient's kidney.

It will be appreciated that various features are sometimes grouped together in a single embodiment, figure, or description thereof for the purpose of streamlining the disclosure. Many of these features may be used alone and/or in combination with one another.

Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "distal" and "proximal" refer to opposite ends of a medical device, including the catheter disclosed herein. As used herein, the distal portion of the catheter is the portion that first enters the patient's body during use, while the proximal portion is a portion at the opposite end, along the longitudinal direction of the catheter.

The term "resilient" refers to a component, device, or object having a particular shape that can then be elastically deformed into a different shape, but that may return to the original shape when unconstrained. For example, a resilient portion of the catheter may have a first shape when unconstrained (i.e., when no exterior force acts upon the catheter) and, in use, the resilient portion may then be constrained (i.e., temporarily engaged with a guidewire) to elastically deform the resilient element into a second shape (i.e., a straightened condition over the guidewire), then unconstrained (i.e., the guidewire is removed, leaving the catheter in position within the kidney) such that the resilient portion returns to its first shape or substantially returns to its first shape.

Figure 5:
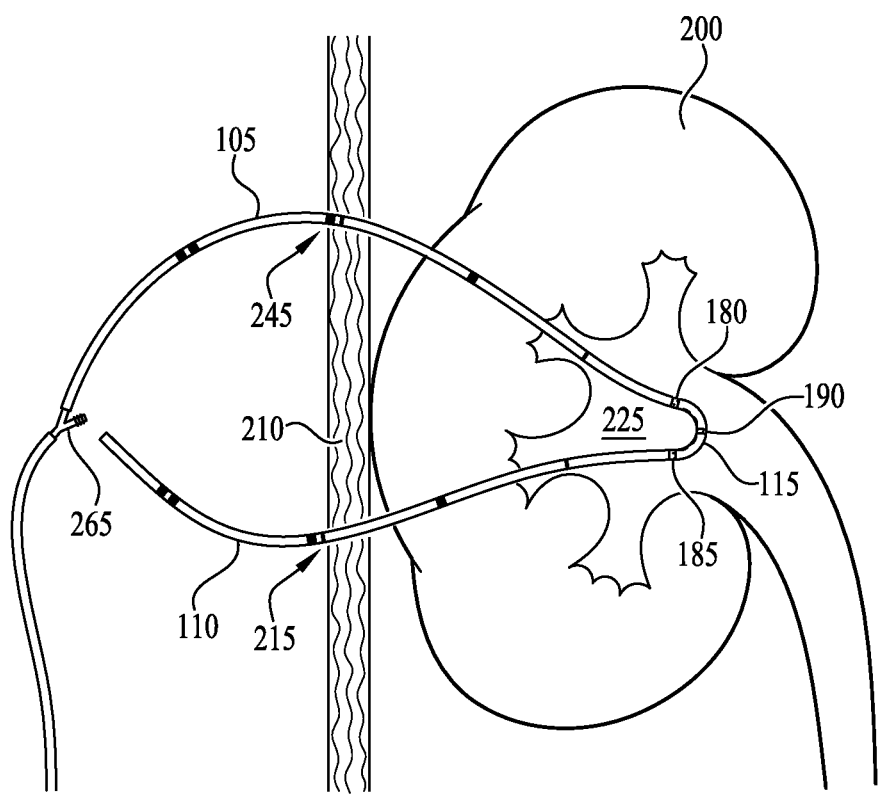
FIG. 5 illustrates the catheter of FIG. 1 in a deployed position.

FIG. 1 illustrates an embodiment of a drainage catheter 100 that may be used for percutaneous nephrostomy for urinary diversion in patients with an obstruction. With general reference to FIGS. 1 and 1A, the drainage catheter 100 includes a distal tube segment 105 and a proximal tube segment 110, the tube segments 105, 110 connected together via an arcuate end portion 115 that may be generally U-shaped. The catheter 100 includes a plurality of drainage bores or openings 175 formed along an inner surface 160 of the U-shaped end portion 115. In some embodiments, the catheter 100 is free of drainage bores on the outer surface 165 to avoid clogging by surrounding kidney tissues or other structures. In an exemplary operation, once the drainage catheter 100 is deployed within the kidney 200, the arcuate end portion 115 sits in the renal pelvis 225, with the tube segment 105, 110 each outwardly through the skin 210 as illustrated in FIG. 5. The tube segments 105, 110 may be connected to a connector 265, which in turn is connected to a drainage bag or other receptacle (not shown) for collecting the drained material. Additional details of the drainage catheter 100 and its operation are provided below with reference to the figures.

It should be understood that while the written description and figures may reference use of the drainage catheter 100 for percutaneous nephrostomy, the disclosed drainage catheter 100 may be used for providing drainage to other organs or anatomical structures as well. Accordingly, the use of the drainage catheter 100 is meant only as an example and is not meant to limit use of the drainage catheter 100 to the kidney.

With reference to FIG. 1, the drainage catheter 100 is a generally elongate, tubular structure that may comprise any one of a variety of resilient and flexible bio-compatible materials, such as silicone rubber, nylon, polyurethane, polyethylene terephthalate (PET), latex, thermoplastic elastomers, or other suitable materials. As mentioned previously, the catheter 100 includes a distal tube segment 105 and a proximal tube segment 110 connected to one another by an arcuate end portion 115 to form a continuous structure with a looped end. A lumen 120 extends through the catheter 100 along a central axis 125 thereof to provide a drainage passageway for fluids exiting the kidney 200. In some embodiments, the lumen 120 may also be used to introduce antibiotics or other fluids into the kidney 200 as needed, such as to treat infections or to provide other medical relief. In some embodiments, a lead-in portion 130 of the distal tube segment 105 may be tapered or angled inwardly toward the central axis 125, with the lead end 135 of the distal tube segment 105 being generally flat, such that the lead-in portion 130 generally resembles a truncated pyramid shape, with the lumen 120 extending there through. As is further described below with reference to FIGS. 2-5, the tapered lead-in portion 130 may be helpful to allow the catheter 100 to track the guidewire 230 during insertion into the kidney 200. In other embodiments, the lead-in portion 130 may not be tapered.

To help ensure safe and accurate placement of the catheter 100 within the kidney 200, the distal and proximal tube segments 105, 110 each include various depth markers 140, 145, 150, 155 printed thereon at predetermined points along the catheter 100, with the depth markers 140, 145, 150, 155 encircling the circumference of the respective tube segments 105, 110 to ensure that the bands are easily identifiable. For example, with particular reference to FIG. 1, the catheter 100 may include a 5-cm band marker 140, a 10-cm band marker 145, a 15-cm band marker 150, and a 20-cm band marker 155, with the respective markers printed on each of the tube segments 105, 110. The position of the depth markers 140, 145, 150, 155 on the distal tube segment 105 mirrors the position of the depth markers 140, 145, 150, 155 on the proximal tube segment 110. In some embodiments, the marking pattern associated with individual band markers may be unique for each particular depth marker to allow a practitioner to quickly determine the depth from the marking pattern alone rather than having to read a number scale or other numerical indicia. It should be understood that the depth values provided in the above description are for illustration purposes only. In other embodiments, the depth for the depth markers may be different than the scale provided. In addition, the number of depth markers printed on the catheter 100 may be more or fewer than the four markers printed on the illustrated embodiment of the catheter 100. In some embodiments, the depth markers may include or be replaced by numeric symbols.

As noted previously, the catheter 100 includes an arcuate end portion 115 connecting the tube segments 105, 110 together to form a continuous structure. With particular reference to FIG. 1A, the arcuate end portion 115 includes an inner surface 160 and an outer surface 165, where the inner surface 160 has a first radius of curvature $R_{inner}$ as measured from a transverse axis 170 generally traversing the catheter 100 at the edges of the arcuate end portion 115. The outer surface 165 has a second radius of curvature $R_{outer}$ measured relative to the transverse axis 170, with $R_{outer}$ being greater than $R_{inner}$.

The inner surface 160 of the arcuate end portion 115 includes a plurality of drainage holes 175 formed thereon, where the drainage holes 175 extend through the inner surface 160 of the catheter 100 and are in communication with the lumen 120 to provide a drainage pathway for antibiotics and other medical fluids into the kidney 200 and waste or other fluids out of the kidney 200. In some embodiments, the outer surface 165 of the catheter 100 is free of any drainage holes to minimize potential blockage and clogging of the drainage holes and maintain patency of the catheter 100 as the kidney tissues collapse around the catheter 100. In other words, the body of the catheter 100 may tend to prevent tissue from collapsing against the drainage holes 175 due to the arcuate shape of the catheter 100, thus preventing clogging and maintaining patency.

The arcuate end portion 115 of the catheter 100 may further include radiopaque marker bands 180, 185, and 190 printed thereon to help ensure optimal placement of the end portion 115 of the catheter 100 for proper drainage. For example, with reference to FIG. 1A, the catheter 100 may include 2-mm marker bands 180, 185 generally mirroring one another on the tube segments 105 and 110 and marking the respective ends of the arcuate end portion 115, and include a 1.5-mm marker band 190 positioned at a general midpoint of the arcuate end portion 115 and along a central axis 195 of the catheter 100 generally perpendicular to the transverse axis 170. In some embodiments, marker bands 180, 185, and 190 may be the same length, for example, 2-mm. In some embodiments, the marker bands 180 and 185 may be aligned on the transverse axis 170. In such embodiments, the marker band 190 may divide the position of the drainage holes 175 to ensure an even distribution on the inner surface 160 of the catheter 100, with the marker bands 180, and 185 bookending the drainage holes 175. In this arrangement, the marker bands 180, 185, and 190 collectively provide precise guidance to determine the position and arrangement of the drainage holes 175 during and after insertion of the catheter 100. In addition, the number of marker bands may be more or fewer than the three marker bands 180, 185, and 190 on the illustrated embodiment of the catheter 100.

In some embodiments, the catheter 100 may include a hydrophilic coating bound to the catheter surface. The hydrophilic coating absorbs and binds water to promote a smooth and slippery surface and help reduce pain, pressure, or discomfort during the insertion and removal process. With reference to FIGS. 2-5, the following sections provide additional details of a process for inserting the catheter 100 during a percutaneous nephrostomy procedure according to one exemplary embodiment. It should be understood that certain steps relating to a percutaneous nephrostomy procedure may not be discussed in detail to avoid obscuring more pertinent aspects of the embodiments. However, one having ordinary skill in the art would nonetheless understand how to effectively implement the disclosed catheter 100 during such medical procedures.

FIGS. 2-5 collectively illustrate an exemplary procedure for guiding and placing the catheter 100 within the kidney 200 during a percutaneous nephrostomy. With reference to FIGS. 2-5, the following sections describe additional details relating to an exemplary deployment and use of the drainage catheter 100. In some embodiments, the drainage catheter 100 may be delivered in accordance with conventional catheterization techniques. Accordingly, specific details relating to such techniques may not be further described herein to avoid obscuring more pertinent details of the embodiments as noted previously.

With particular reference to FIG. 2, a first needle 205 housed within a first introducer sheath 207 is used to puncture the skin 210 at a first insertion site 215. The needle 205 is pushed through a first calyx to access the renal pelvis 225. With the first needle 205 in position, gentle suction may be placed on the needle 205 until urine is aspirated to ensure proper placement. The first needle 205 may be retracted from the first introducer sheath 207 and a guidewire 230 may be advanced through the first introducer sheath 207 and into the renal pelvis 225. In some embodiments, the guidewire 230 may include a hydrophilic coating to help promote easy movement into the renal pelvis 225. In some embodiments, once the guidewire 230 is in position, the first introducer sheath 207 may be retracted, leaving the guidewire 230 in position. Alternatively, the first introducer sheath 207 may be left in position to help manipulate the guidewire 230 as needed to couple with the snare 260 as described below. In some embodiments, the first needle 205 may be used to puncture the skin 210 without the first introducer sheath 207 and the guidewire 230 may be advanced through the first needle 205.

With particular reference to FIG. 3, a second needle 240 housed within a second introducer sheath 242 is used to puncture the skin 210 at a second insertion site 245 and pushed through a second calyx toward the renal pelvis 225. Once the second introducer sheath 242 is in position at the renal pelvis 225 near the guidewire 230, the second needle 240 may be retracted from the second introducer sheath 242. After the second needle 240 is retracted, a second guidewire 255 may be inserted through the second introducer sheath 242 and advanced toward the first guidewire 230. An end of the second guidewire 255 includes a snare or other grasping device 260 that is maneuvered toward the guidewire 230 and coupled thereto, such as via a curved tip end 235. In embodiments where the guidewire 230 does not include a curved tip 235 (e.g., the guidewire 230 may instead have a planar end), the snare 260 may be used to ensnare an end portion of the guidewire 230. Once the snare 260 is coupled to the first guidewire 230, the second guidewire 255 is retracted to advance the first guidewire 230 and create a continuous track extending from the first calyx to the renal pelvis and out the second calyx.

As generally illustrated in FIGS. 4 and 5, the catheter 100 may now be inserted into the kidney 200. With the guidewire 230 in position, the catheter 100 may first be straightened out to generally flatten out the arcuate end portion 115 for insertion. Once the catheter 100 is straightened out, the tapered lead-in portion 130 is first inserted onto the guidewire 230 and advanced into the first calyx, through the renal pelvis 225, and out the second calyx. The catheter 100 is pulled outwardly through the second insertion site 245 until the arcuate end portion 115 is resting in a desired position within the renal pelvis 225. The radiopaque markers 180, 185, 190 may be used to accurately position the drainage holes 175 as desired. In some embodiments, a dilator (not shown) may be advanced over the guidewire 230 prior to insertion of the catheter 100 to dilate the pathway and simplify insertion.

As noted previously, the arcuate end portion 115 may have increased stiffness and resilience such that the arcuate end portion 115 returns to its initial curved configuration once the catheter 100 is free from external forces (see FIG. 5). The curvature of the arcuate end portion 115 and the placement of the drainage holes 175 along the inner surface 160 avoids clogging of the catheter 100 and promotes drainage of the kidney 200 through the lumen 120. In some embodiments, the arcuate end portion 115 is sufficiently stiff and resilient so as to create a bend with a distance D between the distal and proximal tube segments 105 and 110 ranging from approximately 1 cm to 5 cm. In other embodiments, the distance D may instead range from 1 cm to 3 cm. In still other embodiments, the distance D may range from 1.5 cm to 2.5 cm. In yet other embodiments, the distance D may be approximately 2 cm.

With reference to FIG. 5, once the catheter 100 is positioned within the kidney 200 as desired, the first introducer sheath 207 and the second introducer sheath 242 may be removed. In addition, once the catheter 100 is positioned within the kidney 200, one or both tubes 105 and 110 may be cut to a desired length to manage the catheter 100 as needed. For example, in one embodiment, the tapered-lead in portion 130 of the distal tube segment 105 may be cut to size and a connector 265 (or other suitable connector) may be attached to both the distal and proximal tube segments 105 and 110 to direct fluids removed from the kidney 200 to a drainage bag or other receptacle (not shown). In some embodiments, the connector 265 may include a break-away portion that is removable to avoid damage that may be caused to the kidney 200 or other surrounding structures by accidental pulling or removal of the catheter 100. In some embodiments, the connector 265 may include break-away features such as those described in U.S. patent application Ser. No. 15/228,796, the disclosure of which is incorporated herein by reference in its entirety. In other embodiments, the connector 265 may have the same or similar features as the connector 500 shown in FIG. 8 below or the connector 600 shown in FIG. 9.

Figure 6:
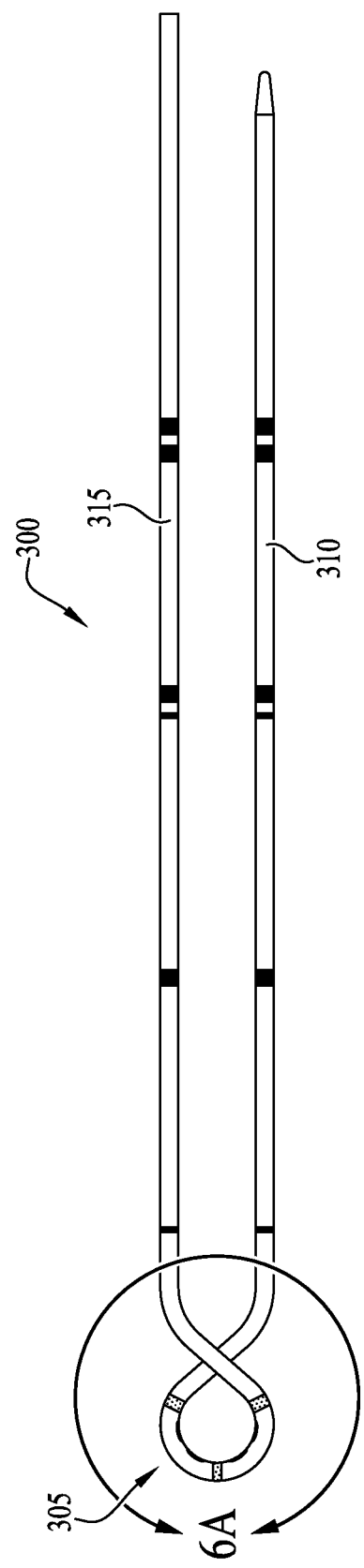
FIG. 6 illustrates a view of a twisted drainage catheter in accordance with another exemplary embodiment.
Figure 6A:
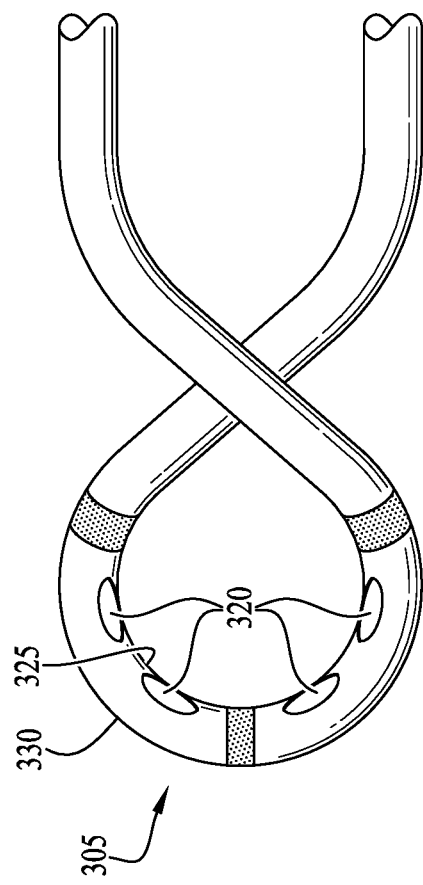
FIG. 6A illustrates an expanded view of an end portion of the twisted drainage catheter of FIG. 6.

Other configurations of the drainage catheter are also contemplated. For example, FIGS. 6 and 6A collectively illustrate another embodiment of a drainage catheter 300 having a looped end portion 305 where the distal tube segment 310 crosses over or underneath the proximal tube segment 315. The drainage catheter 300 may include one or more drainage bores 320 formed along the interior surface 325, with the exterior surface 330 being free of drainage bores 320 in a similar fashion as the catheter 100 of FIG. 1. Similar to the catheter 100 described previously, the catheter 300 is designed with sufficient flexibility and resilience to regain its looped configuration after deployment in a biological structure. The deployment process may be similar as described in FIGS. 2-5 for the catheter 100.

In some embodiments, the catheter 300 may be deployed within the kidney or other similar biological structures. In some instances, the catheter 300 may be deployed within structures with sufficient open space to allow the catheter 300 to return to its looped configuration once deployed. Thus, in some embodiments, once the external forces on the catheter 300 are removed, the catheter 300 may return to its looped configuration. However, in other embodiments, the catheter 300 may not fully regain its looped configuration and instead resemble the deployed shape of catheter 100, due to forces applied by surrounding tissue preventing the catheter 300 from fully regaining its unconstrained shape. In some instances, guidewires or other devices may be used to manipulate the catheter 400 into its looped configuration. In the looped configuration, the body of the catheter 300 may tend to prevent tissue from collapsing against the drainage holes 375 due to the looped shape of the catheter 300, thus preventing clogging and maintaining patency.

FIGS. 7 and 7A collectively illustrate another embodiment of a drainage catheter 400 having a coiled end portion 405. The drainage catheter 400 may include one or more drainage bores 410 formed along the interior surface 415 of the first coiled section 420, with the exterior surface 425 of the first coiled section 420 being free of drainage bores in a similar fashion as the catheter 100 of FIG. 1. Similarly, a second coiled section 430 may include one or more drainage bores 435 formed along an interior surface 440, with an exterior surface 445 being free of drainage bores. Similar to the catheter 100 described previously, the catheter 400 is designed with sufficient flexibility and resilience to regain its coiled configuration after deployment in a biological structure. The deployment process may be similar as described in FIGS. 2-5 for the catheter 100.

Like the catheter 300, catheter 400 may be deployed within the kidney or other biological structures and may be configured for use within structures with sufficient open space to allow the catheter 400 to regain its unconstrained shape. As with catheter 300, guidewires or other devices may be used to manipulate the catheter 400 into its coiled configuration. In the coiled configuration, the body of the catheter 400 may tend to prevent tissue from collapsing against the drainage holes 475 due to the coiled shape of the catheter 400, thus preventing clogging and maintaining patency.

Figure 8:
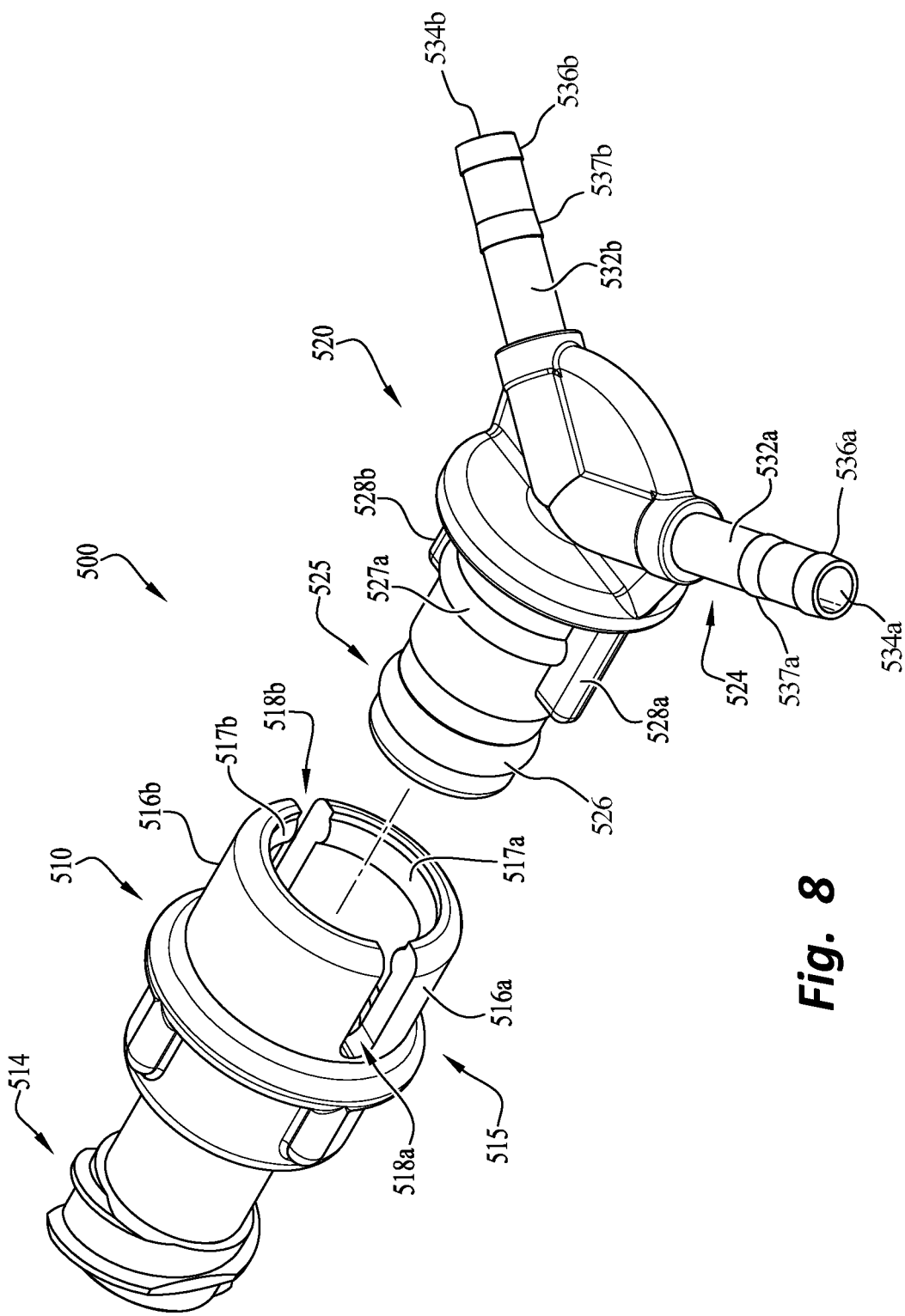
FIG. 8 is a perspective view of a break-away connector that may be used with any of the drainage catheters of FIGS. 1, 6, and 7.

FIG. 8 is a perspective view of a break-away connector 500 in an uncoupled state. As illustrated, the break-away connector 500 includes a first body member 510 and a second body member 520. The first body member 510 includes a coupling end portion 514 and a break-away end portion 515. The coupling end portion 514, as illustrated, comprises a female connector. In other embodiments, however, other suitable coupling mechanisms may also be used. The first body member 510 may further comprise one or more resilient arms, such as a first resilient arm 516a and a second resilient arm 516b. Each of the resilient arms 516a and 516b may comprise one or more ridge portions or raised portions, such as a first ridge portion 517a and a second ridge portion 517b. The first ridge portion 517a and the second ridge portion 517b extend radially inward (internally). The height of the ridge portions 517a and 517b may be varied. Additionally, one or more slots (e.g., a first slot 518a and a second slot 518b) may be disposed adjacent, between, or within the one or more resilient arms 516a, 516b.

The second body member 520 includes a coupling end portion 524 and a break-away end portion 525. The second body member 520 may include an O-ring or seal 526 that seals the first body member 510 and the second body member 520 when coupled. As depicted, the coupling end portion 524 comprises a Y-shaped connector including a pair of legs 532a and 532b. Leg 532a may have a lumen 534a to receive bodily fluids from the catheter 100 when the catheter 100 is attached to the leg 532a. Leg 532b may have a lumen 534b to receive bodily fluids from the catheter 100 when the catheter is attached to the leg 534b. Lumens 534a and 534b may converge to form a single lumen that extends to distal end of the break-away portion 525. Again, as stated above, other suitable coupling mechanisms are also within the scope of this disclosure.

The break-away end portion 525 of the second body member 520 may comprise one or more ribs, such as a first rib 528a and a second rib 528b disposed on an opposite side of the second body member 520 from the first rib 528a. The break-away end portion 525 may further include a first ridge portion or raised portion 527a that extends from the first rib 528a to the second rib 528b. The first ridge portion 527a extends radially outward (externally). The ridge portion 527a may have an arc shape. A corresponding second ridge portion 527b (not shown) may be located on the opposite side of second body member 520 and extend from the second rib 528b to the first rib 528a. The break-away end portion 525 may further include additional ridge portions that are parallel to the ridge portions 527a and 527b. The height of the ridge portions 527a and 527b may be varied.

When the connector 500 is in a coupled configuration, the one or more ribs 528a and 528b are configured to be at least partially disposed within at least a portion of the one or more slots 518a and 518b upon coupling of the first body member 510 and the second body member 520. In addition, the one or more ridge portions 517a and 517b of the first body member 510 may be configured to engage or interact with the one or more ridge portions 527a and 527b of the second body member 520 (i.e., upon coupling of the first and second body members 210, 220). The height of the one or more ridge portions 517a and 517b and the height of the one or more ridge portions 527a and 527b determines the amount of force needed to engage and disengage the first body member 510 and the second body member 520. For example, the taller the ridge portions, more force is needed and the shorter the height, less force is needed.

During use, the break-away connector 500 may receive end portions of a catheter via the legs 532a, 532b extending from the coupling end portion 524 of the connector 500. For example, turning to FIG. 5, the legs 532a, 532b may connect to tube segments 105, 110 of the catheter 100, and the coupling end portion 514 may be attached or otherwise connected to a drainage bag or other receptacle (not shown) to direct fluids removed from the kidney 200 to the drainage bag or other receptacle. Leg 532a may have barbs 536a and 537a to secure tube segment 105 and leg 532b may have barbs 536b and 537b to secure tube segment 110.

One advantage of using the break-away connector 500 is that it is designed to uncouple with relatively little force to avoid injury to the patient in cases of accidental removal of the catheter. In one embodiment, an amount of force needed to uncouple the first body member 510 from the second body member 520 may be less than an amount of force needed to dislodge a suture, or to remove the catheter 100 from the patient to ensure that the break-away connector 500 becomes uncoupled before causing injury to the patient. Additional details of similar break-away connectors are further discussed in U.S. patent application Ser. No. 15/228,796, the disclosure of which was previously incorporated herein by reference in its entirety.

Figure 9:
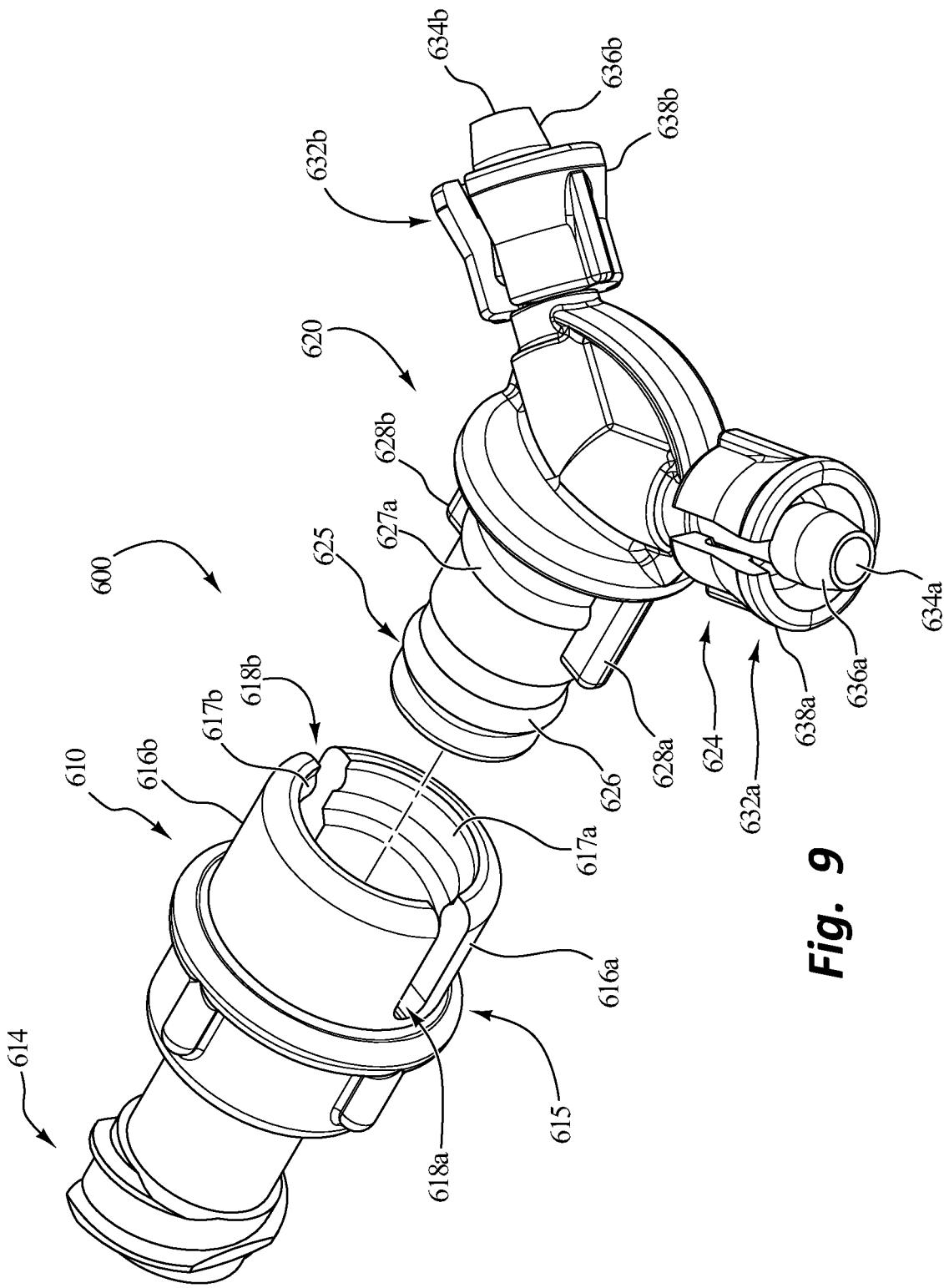
FIG. 9 is a perspective view of a break-away connector that may be used with any of the drainage catheters of FIGS. 1, 6, and 7.

FIG. 9 illustrates an embodiment of a break-away connector 600 that resembles break-away connector 500 descried above in certain respects. Accordingly, like features are designated with like reference numerals, with the leading digits incremented to "6." For example, the embodiment depicted in FIG. 9 includes second body member 620 that may, in some respects, resemble second body member 520 of FIG. 8. Relevant disclosure set forth above regarding similarly identified features thus may not be repeated hereafter. Moreover, specific features of second body member 620 and related components shown in FIG. 9 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the second body member 620 and related components depicted in FIG. 9. Any suitable combination of the features, and variations of the same, described with respect to second body member 520 and related components illustrated in FIG. 8 can be employed with second body member 620 and related components of FIG. 9, and vice versa.

FIG. 9 illustrates a perspective view of a break-away connector 600. Second body member 620 includes a coupling end portion 614 and a break-away end portion 615. The second body member 620 may include an O-ring or seal 626 that seals the first body member 610 and the second body member 620 when coupled. As depicted, the coupling end portion 625 comprises a Y-shaped connector including a pair of legs 632a and 632b. Again, as stated above, other suitable coupling mechanisms are also within the scope of this disclosure.

Leg 632a may include a barb 636a and a collar 638a to secure tube segment 105 to the leg 632a. Collar 638a may be coaxial with the leg 632a. FIG. 10A illustrates leg 632a and tube member 105 in an uncoupled state. In FIG. 10B, tube segment 105 may pass over barb 636a and under collar 638a to secure tube segment to leg 632a. When a force F is applied to the tube segment 105, the collar 638a slides along leg 632a and locks tube member 105 against barb 636a, as illustrated in FIG. 10C. Accordingly, the collar 638a helps secure the tube member to leg 632a. A similar barb 636b and collar 638b may be found on the leg 632b to secure the tube segment 632b.

Tube member 105 may be removed from leg 632a from pulling collar 638a and tube member 105 in different directions.

Some embodiments relate to a kit for establishing a drainage catheter in a patient with a break-away connector. The kit may include, inter alia, the follow components: drainage catheter 100 that includes the tube member 105, the tube member 110, and the arcuate end portion 115, and the break-away connector 500 or 600, with the first body portion 510 or 610, and at least three different second body portions 520 or 620. The at least three different second body portions 520 or 620 include varying heights for the ridge portion 527a and 527b or 627a and 627b. A first ridge portion height may be small, e.g., 5 mm, a second ridge portion height may big, e.g., 15 mm, and a third ridge portion height may be between the first and second heights, e.g., 10 mm. The varying heights of the ridge portion 527a and 527b or 627a and 627b vary the amount of force required to couple and uncouple the break-away connector 500 or 600 to avoid injury to the patient in cases of accidental removal of the catheter 100. The practitioner may select the appropriate second body portion 520 or 620 based on the circumstances for a particular patient. For example, a child may receive the second body portion 520 or 620 with the first ridge portion height, to ensure that the second body portion 520 or 620 uncouples easily because a child may be more likely to move around and accidently get the drainage bag caught. A bedridden patient may receive the second body portion 520 or 620 with the second ridge portion height, because a bedridden patient is less likely to move around and get the drainage bag caught on something, so a higher force may be needed to uncouple the second body portion 520 or 620 may help ensure that accidental uncoupling does not occur. As discussed previously, the varying heights may be found on the ridge portion 517a and 517b or 617a and 617b of first body portion 510 or 620.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially straight" is recited with respect to a feature, it is understood that in further embodiments, the feature can have a precisely straight configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A drainage catheter for use in draining body fluids, the drainage catheter comprising:
a tubular body including a first tube segment and a second tube segment connected at a curved end portion to form a continuous structure, the curved end portion including an inner surface and an outer surface, wherein the first tube segment crosses over the second tube segment forming an overlap and the curved end portion comprises a loop such that a portion of the first tube segment, a portion of the second tube segment, and the entire curved end portion are configured to be disposed within a patient;
a lumen extending through the first tube segment, the second tube segment and the curved end portion of the tubular body;
one or more drainage openings only formed on the loop of the inner surface of the curved end portion, the drainage openings in communication with the lumen to form a passageway for draining body fluids, wherein the outer surface of the curved end portion is free of any drainage openings;
a connector including a first branch configured to be coupled to a proximal end of the first tube segment, a second branch configured to be coupled to a proximal end of the second tube segment, and a third branch configured to be coupled to a drainage tube;
a first radiopaque marker disposed at a first end of the one or more drainage openings;
a second radiopaque marker disposed a second end of the one or more drainage openings; and
a third radiopaque marker disposed at an apex of the loop,
wherein the first and second tube segments each further include depth markers marked thereon to indicate a depth of the drainage catheter during insertion, and wherein the depth markers include a first marking pattern at a first depth distance and a second marking pattern at a second depth distance, the first and second marking patterns being different from one another.

2. The drainage catheter of claim 1, wherein one of the first or second tube segments includes a tapered end opposite the curved end portion.

3. The drainage catheter of claim 2, wherein the drainage catheter further includes an axis extending through the lumen, and wherein the tapered end gradually narrows toward the axis.

4. The drainage catheter of claim 1, wherein the depth markers marked on the first tube segment mirror the depth markers marked on the second tube segment.

5. The drainage catheter of claim 1, wherein the inner surface of the curved end portion has a first radius of curvature relative to a transverse axis of the catheter, and wherein the outer surface of the curved end portion has a second radius of curvature relative to the transverse axis, the second radius of curvature being greater than the first radius of curvature.

6. The drainage catheter of claim 5, wherein the first radiopaque marker and the second radiopaque marker are aligned with the transverse axis.

7. The drainage catheter of claim 1, wherein the first tube segment includes the first radiopaque marker formed thereon and the second tube segment includes the second radiopaque marker formed thereon, and wherein the curved end portion includes the third radiopaque marker formed thereon.

8. The drainage catheter of claim 1, wherein the curved end portion is resilient such that it retains its shape in response to an absence of force.

9. The drainage catheter of claim 1, wherein the tubular body includes a hydrophilic coating layer.

10. The drainage catheter of claim 1, wherein the loop is disposed distal to the overlap.

11. The drainage catheter of claim 1, wherein the loop is disposed proximal to the overlap.

* * * * *